United States Patent [19]

Frey et al.

[11] Patent Number: 4,666,449
[45] Date of Patent: May 19, 1987

[54] HIP JOINT SOCKET

[75] Inventors: Otto Frey, Winterthur, Switzerland; Peter G. Niederer, St. Barbara, Calif.

[73] Assignees: Sulzer Brothers Ltd., Winterthur; Protek AG, Berne, both of Switzerland

[21] Appl. No.: 584,889

[22] Filed: Feb. 29, 1984

[30] Foreign Application Priority Data

Mar. 9, 1983 [CH] Switzerland .............. 1260/83

[51] Int. Cl.⁴ .................................................. A61F 2/34
[52] U.S. Cl. ...................................................... 623/22
[58] Field of Search ............... 3/1.9, 1.91, 1.912, 3/1.913; 128/92 C, 92 CA; 403/135, 140, 122

[56] References Cited

U.S. PATENT DOCUMENTS

| 3,385,616 | 5/1968 | Gottschald | 405/122 |
| 4,410,295 | 10/1983 | Ersoy et al. | 403/135 |
| 4,437,193 | 3/1984 | Oh | 3/1.912 |
| 4,482,266 | 11/1984 | Kaneko | 403/135 |

FOREIGN PATENT DOCUMENTS

| 0053794 | 6/1982 | European Pat. Off. | 3/1.912 |
| 3125174 | 2/1983 | Fed. Rep. of Germany | 3/1.912 |
| 7202254 | 8/1973 | Netherlands | 3/1.912 |
| 465199 | 9/1975 | U.S.S.R. | 623/22 |

Primary Examiner—Richard J. Apley
Assistant Examiner—David Isabella
Attorney, Agent, or Firm—Kenyon & Kenyon

[57] ABSTRACT

The hip joint socket is formed of a socket body of relatively elastic material, for example of plastic, and one or more reinforcement rings which are shrunk fit on the socket body under a prestress. The rings impart rigidity to the hip joint socket. The rings may protrude from the contour of the socket body or may have projections which protrude from the contour of the socket body in order to improve fixation in a cement bed or pelvic cavity.

14 Claims, 5 Drawing Figures

HIP JOINT SOCKET

This invention relates to a hip joint socket.

Heretofore, various types of hip joint sockets have been known, for example as described in Swiss Pat. Nos. 568,753 and 593,045. Generally, these hip joint sockets have been made of plastic, particularly of polyethylene, in order to utilize the sliding properties of the material. Further, since the artificial hip joint sockets constitute a foreign body in human bone and tissue, the volumes of these sockets have generally been kept as small as possible. As a result, this has lead to the construction of relatively thin-walled socket bodies which are relatively flexible and which transmit pelvis movements to the mutually congruent sliding surfaces. These movements, however, can lead to what is called the "cherry pit" effect, that is, the "working" of a solid core (pit) out of a softer material during relative motions therebetween.

Thus, when made of plastic, the socket bodies tend to plastically deform under continuous loads. This, in turn, leads to alterations in the shell surface of the bodies. As a result, the congruence of the shell surface which forms one sliding surface of a joint with the other sliding surface formed by the surface a joint head is disturbed and leads to increased attrition.

Accordingly, one requirement of a hip joint socket is that, as a whole, the socket must be as firm and rigid as possible ao that the socket will not become deformed during movements of the joint. This requirement has lead to a number of constructions where an inner plastic shell is enveloped by an outer shell, generally a metallic shell, and is held therein. Such a construction is described in British Pat. No. 1,215,737. However, while the plastic socket body of such a socket is protected from the direct influence of the pelvis movements, relative movements can occur between the inner socket body and the outer shell which lead to wear between the sliding surfaces. Further, any wearing may permit detritus to lodge between the two sliding surfaces.

Accordingly, it is an object of the invention to provide a rigid hip joint socket which is resistant to pelvis movements and which has the sliding properties of plastic sockets.

It is another object of the invention to provide a rigid hip joint socket which occupies a minimum of space.

It is another object of the invention to provide a hip joint socket in which resistance to wear is increased.

Briefly, the invention provides a hip joint socket which is comprised of a socket body having a hemispherical socket and at least one annular shoulder in an outer shell thereof and at least one closed reinforcement ring disposed on the shoulder and holding the body under a prestress.

The socket body which is generally made of plastic is stiffened by the reinforcement ring so that a rigid and firm socket results. Further, relative movement between the socket body and ring is prevented by the prestress with which the ring sits on the body. Generally, the ring is made of a metal or alloy which is common in implant technology.

The rigidity of the "total" socket can be improved if the flank of each shoulder is conically tapered relative to a central axis of the socket body while the reinforcement ring has a surface mating with the flank and tapered in the same directon, i.e. in an opposite direction to the tapering of the socket. Also, anchoring of the socket is a pelvic bone with a cement bed or in a cement-free manner can be made more effective if a reinforcement ring projects from a contour of a socket body or is provided with an outwardly projecting lug.

These and other objects of the inventin will become more apparent from the following detailed description taken in conjunction with the accompanying drawings wherein.

Figure 1:
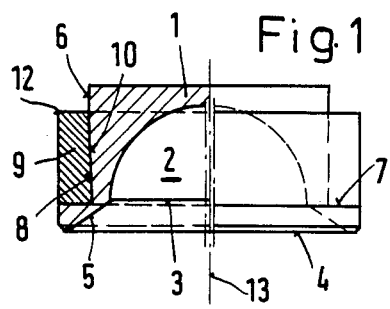
FIG. 1 illustrates a part cross-sectional view of a hip joint socket constructed in accordance with the invention.

Referring to FIG. 1, the implantable hip joint socket includes a socket body 1 which has a cross-section forming an equilateral trapezoid so that the basic form is a truncated cone. As illustrated, the socket body 1 has a hemispherical socket 2 which is disposed about a central axis 13 so as to receive a joint head of a femur head prosthesis (not shown) as well as an annular shoulder 7 in an outer surface 6. As indicated, the base diameter 3 of the hemispherical socket 2 which is in a diametric plane does not coincide with the base 4 of the socket body 1 but is shifted into the socket body 1 relative to the base 4. Further, the socket 2 changes over from the base diameter 3 outwardly into a widening cone 5.

The annular shoulder 7 which is formed in the outer surface or shell 6 of the body 1 has a flank 8 which is conically tapered relative to the central axis 13 of the body 1 in a direction counter to the taper of the socket body 1. That is, the flank 8 is tapered inwardly toward the socket end of the body 1.

The hip joint socket also has a reinforcement ring disposed on the shoulder 7 in the plane of the socket 2 and proximal to the plane of the base diameter 3 which holds the body 1 under a prestress. This reinforcement ring 9 is a closed ring and is "shrink-fitted" in the manner of a barrel hoop onto the body 1 so as to impart great firmness and rigidity to the socket body 1. The ring also has an inside surface or flank 10 which mates with the shoulder flank 8 and which is tapered conically in the same direction as the shoulder flank 8 relative to the central axis 13 of the body 1.

The shrink-fitting of the reinforcement ring 9 can be effected, for example, by a simple pressing on or with the aid of a conventional technique whereby the socket body 1 is, for example, deep-cooled before the ring 9 is fitted. In this respect, the diameter of the ring 9 is somewhat smaller, for example by 0.5 millimeters, than the diameter of the socket body 1 in the region of the shoulder 7 at the "service temperature" so that "while in service" the socket body 1 is kept under a prestress.

Figure 2:
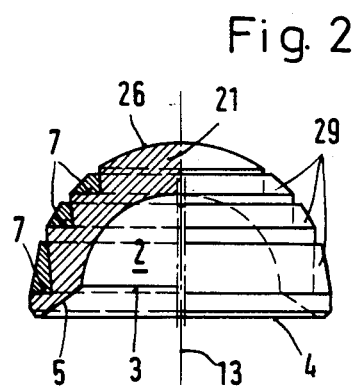
FIG. 2 illustrates a modified hip joint socket having a plurality of reinforcement rings in accordance with the invention.
Figure 3:
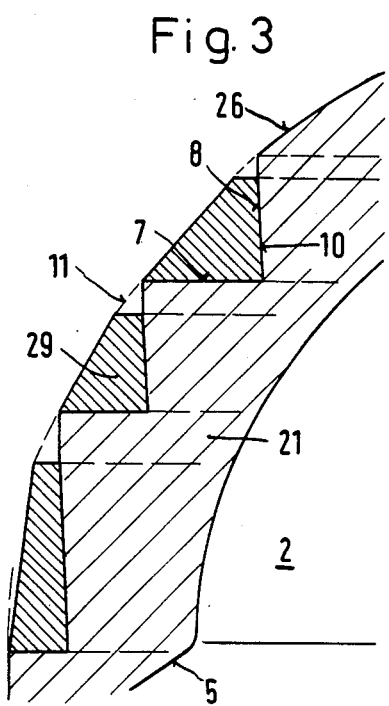
FIG. 3 illustrates an enlarged detail view of the socket of FIG. 2.

Referring to FIGS. 2 and 3, wherein like reference characters indicate like parts as above, the hip joint socket may be formed with a socket body 21 which has a hemispherical outer shell 26. In addition, instead of having one shoulder 7, a plurality of annular shoulders 7 are disposed in the body 1 in stair-like manner at different heights taken in the direction of the central axis 13 as viewed in FIG. 2. In addition, a plurality of discrete reinforcement rings 29, i.e. three are disposed on the socket body 1, one on each shoulder 7. As indicated, the reinforcement rings 29 are of different diameters and are disposed at different heights taken in the direction of the central axis 13. As indicated in FIG. 3, the outer surfaces of the reinforcement rings 29 are adapted to the contoured line 11 of the socket body 21.

Figure 4:
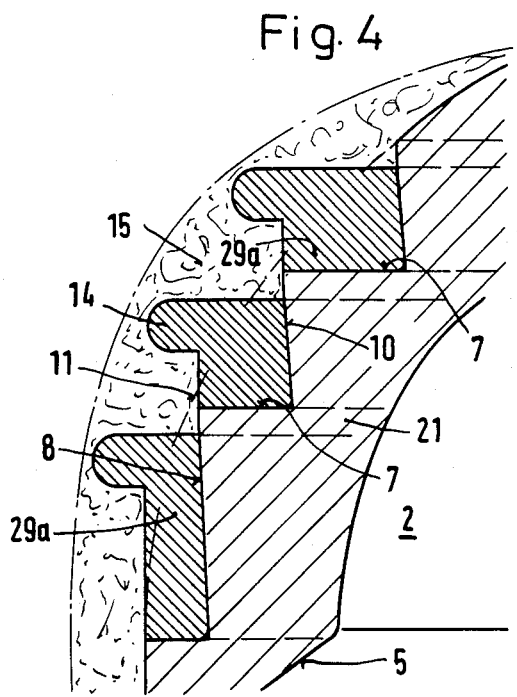
FIG. 4 illustrates a detail view of a modified socket in a cement bed within a pelvic bone in accordance with the invention.

Referring to FIG. 4, wherein like reference characters indicate like parts as above, each reinforcement ring 29a may be provided with an outwardly projecting lug 14 which is adapted to protrude into a cement bed 15 within a pelvic cavity in order to increase the solidity of the anchoring of the hip socket in the cement bed 15.

Figure 5:
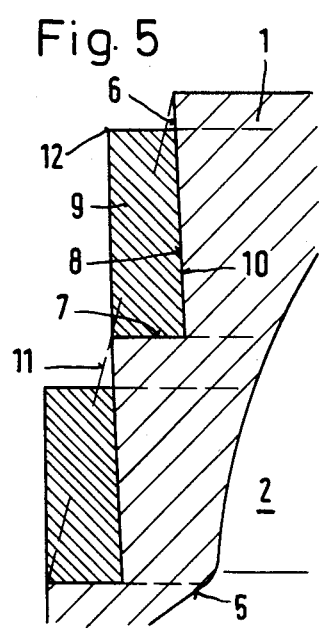
FIG. 5 illustrates a detail of a socket wherein the reinforcing rings project from a contour of the socket body in accordance with the invention.

Referring to FIG. 5, wherein like reference characters indicate like parts as above, a hip socket body 1 may be provided with a pair of shoulders 7 and a pair of reinforcement rings 9. As illustrated, each reinforcement ring 9 protrudes at the outer region from the frusto-conical socket body 1 beyond the contour line 11 of the body 1. The protruding parts of the rings 9 serve to improve the area for anchoring of the total socket and, hence, fixation of the socket. Of note, the corners or edges 12 of the rings 9 are not sharp so as to avoid peak loads which might lead to cracks in the pelvic bone and/or in the cement bed.

A plurality of additional variants are possible for the cross-sectional shape of the reinforcement rings 9 in order to increase the fixation of a socket in a bone or in a cement bed.

The invention thus provides a hip joint socket which is of relatively rigid construction while being of relatively small volume. In addition, the socket has a relatively elastic component in the form of the socket body for receiving a spherical femur head prosthesis while the reinforcement ring imparts rigidity to the socket.

What is claimed is:

1. An implantable hip joint socket comprising
  a socket body having a hemispherical socket for receiving a spherical femur head and having a base diameter in a diametric plane and an outer shell including at least one annular shoulder there, said shoulder having a flank conically tapered relative to a central axis of said body; and
  at least one closed reinforcement ring disposed on said shoulder proximal to said plane and holding said body under a prestress, said ring having a surface mating with said shoulder flank and tapered in the same direction as the tapering of said shoulder flank relative to said central axis.

2. A hip joint socket as set forth in claim 1 wherein said ring projects from a contour of said body.

3. A hip joint socket as set forth in claim 2 wherein said ring has an outwardly projecting lug thereon.

4. An implantable joint socket comprising
  a socket body having a hemispherical socket for receiving a spherical femur head and having a base diameter in a diametric plane and at least one annular shoulder in an outer surface thereof, said shoulder having a flank conically tapered relative to a central axis of said body; and
  a reinforcement ring disposed on said shoulder in the plane of said socket and proximal to said diametric plane with a surface mating with said flank, and ring holding said body under a prestress.

5. A hip joint socket as set forth in claim 4 wherein said body is made of plastic and said ring is made of metal.

6. A hip joint socket as set forth in claim 4 wherein said shoulder flank is tapered inwardly towards the socket end of said body.

7. A hip joint socket as set forth in claim 4 wherein said ring is closed and shrunk-fit on said body.

8. A hip joint socket comprising
  a plastic socket body having a hemispherical socket and a plurality of annular shoulders disposed in stair-like manner in an outer surface thereof; and
  a plurality of metal reinforcement rings, each said ring being disposed on a respective shoulder and holding said body under a prestress.

9. A hip joint socket as set forth in claim 8 wherein each ring projects from a contour of said body.

10. A hip joint socket as set forth in claim 9 wherein at least one ring has an outwardly projecting lug thereon.

11. A hip joint socket as set forth in claim 8 wherein each shoulder has a conically tapered flank and each ring has a tapered surface mating with a respective tapered flank.

12. A hip joint socket comprising
  a socket body having a hemispherical socket and an outer shell including a plurality of annular shoulders disposed in stair-like manner; and
  a plurality of discrete closed reinforcement rings respectively disposed on said shoulders and holding said body under a prestress.

13. A hip joint socket as set forth in claim 12 wherein each said shoulder has a flank conically tapered relative to a central axis of said body and each said ring has a surface mating with a respective shoulder flank.

14. An implantable hip joint socket comprising
  a socket body having a hemispherical socket for receiving a spherical femur head and having a base diameter in a diametric plane and at least one annular shoulder in an outer surface thereof; and
  a closed reinforcement ring shrunk-fit on said shoulder in the plane of said socket and proximal to said diametric plane and holding said body under a prestress.

* * * * *

UNITED STATES PATENT AND TRADEMARK OFFICE
CERTIFICATE OF CORRECTION

PATENT NO. : 4,666,449

DATED : May 19, 1987

INVENTOR(S) : Otto Frey, et al

It is certified that error appears in the above—identified patent and that said Letters Patent is hereby corrected as shown below:

Column 1, line 30 "ao" should be -so-

Signed and Sealed this

Twentieth Day of October, 1987

Attest:

DONALD J. QUIGG

Attesting Officer

Commissioner of Patents and Trademarks